United States Patent [19]

Symon et al.

[11] 3,998,872
[45] Dec. 21, 1976

[54] PREPARATION OF UNSATURATED CARBONYL COMPOUNDS

[75] Inventors: Ted Symon, Lombard; Nils J. Christensen, Palatine, both of Ill.

[73] Assignee: Universal Oil Products Company, Des Plaines, Ill.

[22] Filed: Oct. 5, 1970

[21] Appl. No.: 78,290

[52] U.S. Cl. .................... 260/483; 260/410.9 R; 260/485 R; 260/590 E; 260/597 R
[51] Int. Cl.$^2$ .................. C07C 67/30; C07C 69/73
[58] Field of Search .......... 260/483, 485 R, 597 R, 260/410.9 R

[56] References Cited
OTHER PUBLICATIONS

Bull. of Chem. Soc. of Japan, V.45, 1183–1191 (1972).

Primary Examiner—Vivian Garner
Attorney, Agent, or Firm—James R. Hoatson, Jr.; Raymond H. Nelson

[57] ABSTRACT

Unsaturated carbonyl compounds, and particularly α-substituted allylic carbonyl compounds as exemplified by 3-(1-methylallyl)-2,4-pentanedione are prepared by reacting a conjugated diolefinic compound with a compound possessing an active methylene group in the presence of certain catalytic compositions of matter at a temperature of from about −20° C. to about 150° C. The desired products are useful as intermediates in preparing chemical compounds which possess desirable fragrances.

4 Claims, No Drawings

PREPARATION OF UNSATURATED CARBONYL COMPOUNDS

This invention relates to a process for the preparation of carbonyl compounds and specifically to a method for preparing α-substituted allylic carbonyl compounds by reacting certain diolefinic compounds with compounds possessing an active methylene group in the presence of certain catalysts of the type hereinafter set forth in greater detail.

The products which are prepared according to the process of this invention are useful in the chemical industry and particularly the aroma industry, the compounds thus prepared being useful as intermediates in the preparation of aroma chemicals. The use of synthetically prepared chemical compounds which possess pleasant and fragrant odors is becoming increasingly more important inasmuch as the aroma industry, by utilizing these compounds, will not be subject to the whims and vagaries of nature for supplying the natural products which possess identical odors. The resultant chemical compounds which are prepared from the intermediates of the present invention are useful in the preparation of fragrant or aroma compounds which are added to cosmetic and toiletry articles such as perfumes, colognes, soaps, talcs, bath powders, etc., whereby the aforementioned compositions will possess desirable and pleasing scents. As an example of this, 2-methyl-2-heptene-6-one is an important intermediate for the preparation of citral, citronellol, linalool, and the terpene essential oils, as well as being an intermediate in the preparation of Vitamin A.

It is therefore an object of this invention to provide a process for preparing certain carbonyl compounds which are useful in the chemical industry.

A further object of this invention is to provide a process for preparing α-substituted allylic carbonyl compounds utilizing a catalyst system of a type hereinafter set forth in greater detail.

In one aspect an embodiment of this invention resides in a process for the preparation of an α-substituted allylic carbonyl compound which comprises reacting a conjugated diolefinic compound with a compound possessing an active methylene group in the presence of a catalyst system comprising a palladium-containing compound and a phosphine or phosphite compound at reaction conditions, and recovering the resultant α-substituted allylic carbonyl compound.

A specific embodiment of this invention is found in a process for the preparation of an α-substituted allylic carbonyl compound which comprises reacting 1,3-butadiene with 2,4-pentanedione in the presence of a catalyst system comprising palladium acetylacetonate and tributylphosphine at a temperature in the range of from about −20° C. to about 150° C. and a pressure in the range of from about atmospheric to about 1000 atmospheres, and recovering the resultant 3-(1-methylallyl)-2,4-pentanedione, 3,3-di-(1-methylallyl)-2,4-pentanedione, 3-crotyl-2,4-pentanedione and 3,3-dicrotyl-2,4-pentanedione.

Other objects and embodiments will be found in the following further detailed description of the present invention.

As hereinbefore set forth, the present invention is concerned with the process for preparing unsaturated carbonyl compounds and more specifically α-substituted allylic carbonyl compounds. These compounds are prepared by reacting a diolefinic compound, and particularly a conjugated diolefinic hydrocarbon with a compound containing an active methylene group, said reaction being effected in the presence of certain catalytic compositions of matter of a type hereinafter set forth in greater detail. The process is effected at reaction conditions which will include a temperature in the range of from about −20° C. up to about 150° C. or more and a pressure in the range of from about atmospheric to about 1000 atmospheres or more. In the preferred embodiment, the invention is effected at ambient temperature and atmospheric pressure, however, if superatmospheric pressures are to be employed, said pressure is provided for by the introduction of a substantially inert gas such as nitrogen into the reaction zone. The reactants are usually present in a mol ratio whereby a desired product may be obtained. For example, if a di-substituted product is desired, the diolefinic compound is in excess over the amount of compound containing an active methylene group, the compounds usually being present in a mol ratio of about 1.2:1 to about 2:1 mols of diolefinic compound per mol of compound possessing a methylene group. Conversely, if a mono-substituted product is desired the compound containing the active methylene group is present in a mol excess over the diolefinic compound in a similar range.

Examples of diolefinic compounds, and particularly conjugated diolefinic hydrocarbons will include straight chain conjugated diolefinic hydrocarbons such as 1,3-butadiene, 1,3-pentadiene, 1,3-hexadiene, 2,4-hexadiene, 1,3-heptadiene, 2,4-heptadiene, 1,3-octadiene, 2,4-octadiene, 1,3-nonadiene, 2,4-nonadiene, 3,5-nonadiene, 1,3-decadiene, 2,4-decadiene, 3,5-decadiene, etc.; branched chain diolefinic hydrocarbons such as 2-methyl-1,3-butadiene(isoprene), 2,3-dimethyl-1,3-butadiene, 2,3-diethyl-1,3-butadiene, 2-methyl-1,3-pentadiene, 3-methyl-1,3-pentadiene, 2,3-dimethyl-1,3-pentadiene, 2-methyl-1,3-hexadiene, 3-methyl-2,4-hexadiene, 2-methyl-1,4-hexadiene, 2,5-dimethyl-1,3-hexadiene, 2-methyl-1,3-heptadiene, 2-methyl-2,4-heptadiene, 2-methyl-1,3-octadiene, 2-methyl-2,4-octadiene, 2,7-dimethyl-1,3-octadiene, 2-methyl-6-methylene-2,7-octadiene, 2-methyl-1,3-nonadiene, 2-methyl-1,3-decadiene, etc. It is to be understood that the aforementioned diolefinic hydrocarbons are only representative of the class of compounds which may be used and that the present invention is not necessarily limited thereto.

Examples of compounds possessing active methylene groups which may be effected with the aforementioned conjugated diolefinic hydrocarbons will include such compounds as methyl acetoacetate, ethyl acetoacetate, n-propyl acetoacetate, isopropyl acetoacetate, n-butyl acetoacetate, amyl acetoacetate, hexyl acetoacetate, heptyl acetoacetate, etc., methyl propioacetate, ethyl propioacetate, n-propyl propioacetate, isopropyl propioacetate, n-butyl propioacetate, amyl propioacetate, hexyl propioacetate, hetpyl propioacetate, etc., methyl butyroacetate, ethyl butyroacetate, n-propyl butyroacetate, isopropyl butyroacetate, n-butyl butyroacetate, amyl butyroacetate, hexyl butyroacetate, heptyl butyroacetate, etc., dimethyl malonate, diethyl malonate, dipropyl malonate, dibutyl malonate, dipentyl malonate, etc.; β-diketones possessing the generic formula:

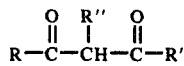

in which R and R' comprise alkyl containing compounds from 1 to about 4 carbon atoms and R" is selected from the group consisting of hydrogen, alkyl, cycloalkyl, aryl, alkaryl and aralkyl radicals such as 2,4-pentanedione, 2,4-hexanedione, 2,4-heptanedione, 2,4-octanedione, 3,5-heptanedione, 3,5-octanedione, 3,5-nonanedione, 4,6-nonanedione, 3-methyl-2,4-pentanedione, 3-ethyl-2,4-pentanedione, 3-cyclopentyl-2,4-pentanedione, 3-phenyl-2,4-pentanedione, 3-benzyl-2,4-pentadione, 3-p-tolyl-2,4-pentanedione, 3-methyl-2,4-hexanedione, 3-cyclopentyl-2,4-hexanedione, 3-phenyl-2,4-hexanedione, 4-ethyl-3,5-heptanedione, 4-p-tolyl-3,5-heptanedione, 4-cyclohexyl-3,5-nonanedione, 4-propyl-3,5-nonanedione, etc.; benzyl ketones such as methyl benzyl ketone, ethyl benzyl ketone, propyl benzyl ketone, butyl benzyl ketone, etc. As in the case of the diolefinic hydrocarbons, it is also understood that the aforementioned compounds containing an active methylene group are also representative of the class of compounds which may be used and that the present invention is not necessarily limited thereto.

The reaction between the conjugated diolefinic hydrocarbon and the compound which possesses an active methylene group is effected in the presence of a catalyst system which comprises a compound containing palladium and a phosphine or phosphite compound. Examples of palladium containing compounds which may be used in the process of this invention will include organo-palladium salts such as palladium acetate, palladium propionate, palladium butyrate, palladium acetylacetonate, etc. It is also contemplated that palladium salts of inorganic acids such as palladium chloride, palladium bromide, palladium iodide, palladium nitrate, palladium sulfate, palladium phosphate, etc., may also be utilized as long as a basic compound such as sodium acetate, potassium acetate, lithium acetate, etc., is also present. It is also contemplated that other palladium containing compounds such as a complex between a palladium salt and an organic ligand in which the ligand portion comprises a tertiary nitrogen containing radical may be utilized in the process of this invention, illustrative examples of these compounds being nitriles such as benzonitrile, propionitrile, acetonitrile, toluonitrile, etc.; heterocyclic tert-nitrogen compounds such as pyridine, quinoline, isoquinoline, picoline, etc.; and tert-aliphatic amines such as triethylamine, tributylamine, etc. Specific examples of these complexes would include dibenzonitrilepalladium dichloride, dipropionitrilepalladium dichloride, etc. Yet another type of palladium containing compound which may also be used as a catalyst includes the π-allyl palladium salts such as the chlorides, bromides, iodides, etc.

Some specific examples of the second component of the catalyst which comprises a phosphine or phosphite compound which may be used include the trialkyl substituted phosphines such as trimethylphosphine, triethylphosphine, tripropylphosphine, tributylphosphine, triamylphosphine, lauryldimethylphosphine, etc.; tricycloalkylphosphines such as tricyclopentylphosphine, tricyclohexylphosphine, tricycloheptylphosphine, etc.; triaryl substituted phosphines such as triphenylphosphine, tribenzylphosphine, tris(p-tolyl)phosphine, tris(p-chlorophenyl)phosphine, tris(2,5-dimethylphenyl)phosphine, etc.; the corresponding phosphite compounds such as trimethylphosphite, triethylphosphite, tripropylphosphite, tributylphosphite, etc.; tricyclopentylphosphite, tricyclohexylphosphite, tricycloheptylphosphite, etc.; triphenylphosphite, tribenzylphosphite, tri-(p-tolyl)phosphite, etc. The components of the catalyst composition will be present in a mol ratio of from about 1:1 to about 1:10 mols of palladium salt per mol of phosphine or phosphite compounds. It is to be understood that the aforementioned palladium containing compounds and phosphine or phosphite compounds are only representative of the type of compounds which may be used, and that the present invention is not necessarily limited thereto.

The process of this invention may be effected in any suitable manner and may comprise a batch or continuous type operation. For example, when a batch type operation is used, a quantity of the starting materials comprising the conjugated diolefinic hydrocarbon and the compound containing an active methylene group are placed in an appropriate apparatus along with a predetermined amount of the catalyst system. If the reaction is to be effected at ambient temperature and atmospheric pressure, the reaction vessel may comprise a flask. However, if elevated temperatures and superatmospheric pressures are to be employed to effect the reaction, the reactor may comprise an autoclave of the rotating or stirring type. The reaction is then allowed to proceed at the predetermined reaction conditions for a residence time which may range from about 0.5 up to about 16 hours or more in duration, said time being dependent upon the particular reaction conditions of temperature and pressure which are employed as well as the reactants which are utilized. Upon completion of the aforementioned residence time, the reaction mixture is recovered from the apparatus and subjected to conventional means of separation whereby the desired α-substituted allylic carbonyl compound is recovered, said conventional means of separation including filtration, washing, drying, extraction, fractional distillation, etc.

It is also contemplated that the process of this invention may be effected in a continuous manner of operation. When such a type of operation is used, the reactants comprising the conjugated diolefinic hydrocarbon and the compound containing an active methylene group are continuously charged to the reaction zone which is maintained at the proper operating conditions of temperature and pressure. In one embodiment, the reactants may be charged to the reaction zone through a separate line, or if so desired, they may be admixed in the reaction zone and charged thereto in a single stream. Likewise, the catalyst system is also charged to the reaction zone through a separate line or it may be admixed with one or both of the reactants before entry into said zone. Upon completion of the desired residence time, the reactor effluent is continuously withdrawn and subjected to conventional means of separation whereby the desired α-substituted allylic carbonyl compound is recovered, while the unreacted starting materials and bottoms from the distillation which are catalytically active are recycled to form a portion of the feed stock.

Some examples of α-substituted allylic carbonyl compounds which may be prepared according to the process of this invention will include 3-(1-methylallyl)-2,4-pentanedione, 3,3-di-(1-methylallyl)-2,4-pentanedione, 3-crotyl-2,4-pentanedione, 3,3-dicrotyl-2,4-pentanedione, 4-(1-methylallyl)-3,5-heptanedione, 4,4-di-(1-methylallyl)-3,5-heptanedione, 4-crotyl-3,5-heptanedione, 4,4-dicrotyl-2,5-heptanedione, dimethyl 2-(1-methylallyl)malonate, dimethyl 2,2-di-(1-methylallyl)malonate, 2-crotylmalonate, 2,2-dicrotylmalonate, ethyl 2-(1-methylallyl)acetoacetate, ethyl 2-crotyl acetoacetate, ethyl 2,2-dicrotyl acetoacetate, methyl-α-crotylbenzyl ketone, methyl-α,α-dicrotylbenzyl ketone, methyl α-(1-methylallyl)benzyl ketone, methyl α,α-di(1-methylallyl)benzyl ketone, ethyl α-crotylbenzyl ketone, ethyl α,α-dicrotylbenzyl ketone, ethyl α-(1-methylallyl)benzyl ketone, ethyl α,α-di-(1-methylallyl)benzyl ketone, propyl α-crotylbenzyl ketone, propyl α,α-dicrotylbenzyl ketone, propyl α-(1-methylallyl)benzyl ketone, propyl α,α-di-(1-methylallyl)benzyl ketone. It is to be understood that the α-allylic carbonyl compounds are only representative of the class of compounds which may be prepared according to the process described herein, and that the present invention is not necessarily limited thereto.

The following examples are given to illustrate the process of the present invention which, however, are not intended to limit the generally broad scope of the present invention in strict accordance therewith.

EXAMPLE I

In this example 10 g. of 1,3-butadiene and 24 g. of 2,4-pentanedione along with a catalyst system consisting of 0.6 g. of palladium acetylacetonate and 2.0 g. of tributylphosphine were placed in a rotating autoclave which was sealed and purged with nitrogen. The mixture was stirred and allowed to remain at room temperature for a period of 16 hours. At the end of this time, the autoclave was opened, it being determined that all of the 1,3-butadiene had reacted with the 2,4-pentanedione. Analysis by means of gas-liquid chromatography determined the presence of a mixture of 3-(1-methylallyl)-2,4-pentanedione, 3,3-di-(1-methylallyl)-2,4-pentanedione, 3-crotyl-2,4-pentanedione, and 3,3-dicrotyl-2,4-pentanedione, the major portion of the product consisting of the monosubstituted dicarbonyl compounds with only minor amounts of the disubstituted compounds being present.

EXAMPLE II

A mixture consisting of 10 g. of 1,3-butadiene, 29 g. of dimethyl malonate and a catalyst consisting of 0.6 g. of palladium acetylacetonate and 5.0 g. of tributylphosphine was placed in the glass liner of a rotating autoclave. The autoclave was sealed, purged with nitrogen and heated to a temperature of 100° C. for a period of 2 hours. During the heating period, the pressure dropped from 91 pounds per square inch to 10 pounds per square inch. At the end of the aforementioned 2 hour period, heating was discontinued and the autoclave allowed to return to room temperature. The excess pressure was discharged, the autoclave was opened and the reaction mixture subjected to gas-liquid chromatography analysis. This analysis disclosed the presence of a mixture of dimethyl 2-(1-methylallyl)malonate, dimethyl 2,2-di-(1-methylallyl)malonate, dimethyl 2-crotylmalonate, and dimethyl 2,2-dicrotylmalonate, the major portion of the product consisting of the mono-substituted compounds.

EXAMPLE III

A mixture comprising 10 g. of 1,3-butadiene, 26 g. of ethyl acetoacetate and a catalyst system consisting of 0.6 g. of palladium acetylacetonate and 2 g. of tributylphosphine was sealed in an autoclave which was thereafter purged with nitrogen. The mixture was stirred and allowed to remain at room temperature for a period of 16 hours. At the end of this time, the autoclave was opened and it was determined that all of the 1,3-butadiene had reacted. A gas-liquid chromatography analysis of the reaction mixture disclosed the presence of ethyl 2-(1-methylallyl)acetoacetate, ethyl 2,2-di-(1-methylallyl)acetoacetate, ethyl 2-crotylacetoacetate, and ethyl 2,2-dicrotylacetoacetate, the major portion of the product consisting of ethyl 2-(1-methylallyl)acetoacetate and ethyl 2-crotylacetoacetate.

EXAMPLE IV

In a similar manner a mixture consisting of 10 g. of 1,3-butadiene, 25 g. of methyl benzyl ketone and a catalyst system consisting of 0.6 g. of palladium acetylacetonate and 2 g. of tributylphosphine was placed in an autoclave which was thereafter sealed and purged with nitrogen. Upon completion of the nitrogen purge, the autoclave was heated to a temperature of 120° C. and maintained thereat for a period of 4 hours. At the end of the 4 hour period, the autoclave was opened and the reaction mixture was recovered. Analysis of the mixture by means of a gas-liquid chromatography disclosed the presence of methyl α-(1-methylallyl)benzyl ketone, methyl α,α-di-(1-methylallyl)benzylketone, methyl α-crotylbenzyl ketone, and methyl α,α-dicrotylbenzyl ketone, the mono-substituted ketones being present in a major portion of the product.

EXAMPLE V

In this example a mixture of 17 g. of 2-methyl-1,3-butadiene (isoprene) and 15 g. of 2,4-pentanedione along with a catalyst system comprising 0.6 g. of palladium acetylacetonate and 4 g. of tri-n-octylphosphine was treated in a manner similar to that set forth in Example I above at a temperature of 120° C. for a period of 2 hours. The reaction product comprised a mixture of 3-(3-methylcrotyl)-2,4-pentanedione, 3-(2-methylcrotyl)-2,4-pentanedione, 3,3-di-(3-methylcrotyl)-2,4-pentanedione and 3,3-di-(2-methylcrotyl)-2,4-pentanedione. Inasmuch as the isoprene was present in the reaction mixture in a mol excess over the 2,4-pentanedione, the major portion of the product consisted of the di-substituted 2,4-pentanedione with only a minor portion of mono-substituted products being present.

We claim as our invention:

1. A process for the preparation of an allylic carbonyl compound which comprises reacting, at a temperature of from about −20° C. to about 150° C. and a pressure of from about atmospheric to about 1000 atmospheres, a conjugated diolefinic hydrocarbon with a compound possessing an active methylene group selected from the group consisting of alkyl acetoacetate, propioacetate and butyroacetate having an alkyl group of from 1 to 7 carbon atoms, in the presence of a catalyst system consisting essentially of a palladium compound and a trihydrocarbyl phosphine or phosphite, said compound possessing an active methylene group being present in a mol excess over said diolefinic hydrocarbon in a mol ratio of about 1.2:1 to about 2:1 mols of said compound possessing an active methylene group to said diolefinic hydrocarbon, and recovering the resultant allylic carbonyl compound.

2. The process of claim 1 in which said compound possessing an active methylene group is an alkyl acetoacetate.

3. The process of claim 1 in which said compound possessing an active methylene group is ethyl acetoacetate and said diolefinic hydrocarbon is 1,3-butadiene.

4. The process of claim 1 in which said catalyst system consists essentially of palladium acetylacetonate and tributylphosphine.

* * * * *